United States Patent [19]

Coleman et al.

[11] Patent Number: 4,551,129
[45] Date of Patent: Nov. 5, 1985

[54] TECHNIQUE AND APPARATUS FOR INTRAOCULAR AND MICROSURGERY INCLUDING LIGHTER-IRRIGATOR HYPODERMIC TUBE

[76] Inventors: D. Jackson Coleman, 515 E. 71st St., New York, N.Y. 10021; Donald E. Orcutt, 3 Honeyman Dr., Succasunna, N.J. 07876; Herbert Berkowitz, 50 Lenox Ter., West Orange, N.J. 07052

[21] Appl. No.: 483,279

[22] Filed: Apr. 8, 1983

[51] Int. Cl.⁴ .................. A61B 17/36; A61B 5/02
[52] U.S. Cl. ................................ 604/21; 604/93; 128/303.1
[58] Field of Search ............... 604/21, 93, 118, 122, 604/257, 290, 294; 128/303.1

[56] References Cited

U.S. PATENT DOCUMENTS

| | | | |
|---|---|---|---|
| 1,939,413 | 12/1933 | Robinson | 604/21 |
| 1,968,997 | 8/1934 | Drucker | 604/21 |
| 3,498,286 | 3/1970 | Polanyi et al. | 604/21 |
| 3,821,510 | 6/1974 | Muncheryan | 604/21 |
| 3,866,599 | 2/1975 | Johnson | 604/21 |
| 3,918,439 | 11/1975 | Zimmer | 128/303.1 |
| 3,982,541 | 9/1976 | L'Esperance, Jr. | 128/303.1 |
| 4,019,514 | 4/1977 | Banko | 604/118 |
| 4,041,947 | 8/1977 | Weiss et al. | 604/118 |
| 4,311,138 | 1/1982 | Sugarman | 604/21 |
| 4,422,719 | 12/1983 | Orcutt | 40/547 |

Primary Examiner—C. Fred Rosenbaum
Assistant Examiner—Gene B. Kartchner
Attorney, Agent, or Firm—Laughlin & Markensohn

[57] ABSTRACT

A technique and system for facilitiating intraocular and other microsurgery comprising a lighter-irrigator tube which utilizes a central light guide to conduct light into the area of the surgery along the fluid infusion pathway. An auxiliary to the lighter-irrigator comprises a fiber optic work cord or light pipe characterized by light transmission and light dispersion along its path between a light source and the lighter-irrigator, and which may be utilized alone, or with other similar auxiliary cords, to provide low level lighting to the work areas, so that adequate work light is provided for the surgical assistants and aneasthesiologists, while maintaining maximum visualization for the surgeon.

20 Claims, 7 Drawing Figures

TECHNIQUE AND APPARATUS FOR INTRAOCULAR AND MICROSURGERY INCLUDING LIGHTER-IRRIGATOR HYPODERMIC TUBE

BACKGROUND OF THE INVENTION

This invention relates to a system including an intraocular work light for use during vitreous surgery which provides a pathway for infusion of fluid into the eye during surgery.

The most widely accepted prior art means for performing intraocular surgery comprises a bimanual technique for irrigation, visualization, and suction cutting of intraocular membranes. This prior art technique provides two ports for instrument exchange, and for utilizing two instruments with optimum attitudinal approach to tissue, as well as illumination of structures. It is customary for the surgeon in carrying out this technique to hold a suction cutter in one hand, with a light in the other. A third separate device comprising an infusion port is required in order to maintain adequate flow of fluid into the eye to maintain intraocular volume during surgery.

Instruments have been described by T. A. Pool and R. D. Sudarsky, 88 *American Journal of Opthalmology* 1093-1095 (1979), and by S. M. Meyers, R. F. Bonner and S. B. Leighton, 100 *Arch Opthalmology*, April 1982, which combine the water infusion and light conducting elements in a single probe. Although such techniques eliminate the third portal for infusion, they have the disadvantage that the infusion volume is reduced by the physical limitations imposed by combining two conducting systems side by side while maintaining the small instrument size. This problem cannot be solved by increasing the intraocular illumination because of the danger of producing retinal change.

Furthermore, it has been found that ambient room light during vitreous surgery reduces the efficient utilization of intraocular illumination, and can prove to be distracting to the surgeon. The reduced level of ambient lighting which may be desirable for optimum performance by the eye surgeon, may be insufficient for the surgical assistants to function properly.

Another problem which may arise in the use of complex and multiple-element surgical tools is that of sterilization, which tends to increase the cost of the procedure by requiring that each element be resterilized or discarded after each use.

BRIEF DESCRIPTION OF THE INVENTION

It is therefore a principal object of the invention to provide improvements in intraocular and other types of microsurgery requiring liquid infusion, more particularly by a method and apparatus which allows light to travel along the fluid path, thereby maintaining adequate light while increasing the space available for fluid flow.

Another object of this invention is to reduce the number of surgical openings needed in the eye while maintaining full infusion volume of liquid into a small port opening.

It is another object of this invention to provide techniques and apparatus for intraocular illumination during surgery which allow the surgeon to maintain maximum visualization while providing adequate work light for surgical nurses, assistants and anaesthesiologists.

A further object of the invention is to provide techniques and apparatus for intraocular and other types of microsurgery in which the equipment can be simply and inexpensively re-sterilized and re-used, or, because of its inexpensive cost, discarded after each use.

These and other objects of the invention can be found in a combination with a low level lighting system particularly adapted for use in intraocular and other types of microsurgery, a salient feature of which is a lighter-irrigator tube which utilizes a central light guide to conduct light along the fluid infusion pathway. The lighter-irrigator tube of the present invention utilized a central strand of optical fiber material to serve as a light guide in order to maximize the light coupling and flux through the fluid medium. The irrigator of the present invention comprises a cannula which is attached to a light source by a fiber optic work cord or light pipe characterized by a new type of light transmission and light dispersion along its path, the rate of light dispersion being controllable during its process of manufacture. The cannula comprises an exceptionally thin wall so as to allow the maximum possible clearance for light and water transmission to the eye. The cannula hub has a short tube attached to a lateral wall for irrigation fluid to be passed into a hypodermic tube, for transmission in a direction parallel to the light guide. Such fluid is preferably a prescribed balanced salt solution from a supply reservoir connected to the cannula hub, which may comprise a hanging bottle source.

The light from the fiber optic light pipe, comprising a light transmission and dispersion cord, is transmitted into the standard cannula hub, wherein the rays of light are picked up from the light pipe by means of a microlens and funneled into a small singlefiber light guide which transmits the light down through the distal end of the tube to the globe of the eye. The distal end of the tube may comprise either a convex or concave lens, or it may be flat for flush contact.

In accordance with a further feature of the present invention, a fiber optic light pipe comprising a light transmissiona and dispersion cord may be used to provide a source of light for the surgical staff that does not appreciably interfere with the surgeon's dark adaptation. In accordance with a preferred example, the fiber optic light pipe comprises a tetrafluoroethylene-coated thermoset polycarbonate "fiber optic" bundle. As stated, this is configured so that light traveling from a light source is transmitted through the fiber optic bundle comprising the light pipe into the cannula of the irrigator light through a lens, from whence it travels through a light funnel, into the thin plastic light guide encased in a hypodermic tube, and out the end of the tube, to supply light into the posterior globe of the eye.

Water solution to maintain the pressure in the globe of the eye enters from an inlet pipe connected to a source of a suitable solution, passing into a cannula hub, from which it enters a hypodermic tube through a pair of holes in the side of the tube. The water solution then travels alongside the fiber optic light guide to the distal end of the hypodermic tube where it is discharged through a pair of holes on the sides at the tip of the tube. The fiber optic light guide, which is formed from a single piece of material, collects light in the large-lensed end, from which it travels within the funnel which serves to concentrate a relatively large amount of light into the small light guide tube. The light being emitted from the hypodermic tube lights up the whole end, and may be manually focused on the operating area by the operating surgeon.

These and other objects, features and advantages of the invention will be better understood from a detailed study of the specification hereinafter with reference to the attached drawings.

SHORT DESCRIPTION OF THE DRAWINGS

FIG. 6 shows the optical light guide removed from the cannula and hypodermic tube of the present invention.

FIG. 6a shows the optical light guide removed from the cannula and hypodermic tube of the present invention with a concave lens substituted for the convex lens of FIG. 6.

DETAILED DESCRIPTION OF THE INVENTION

Figure 1:
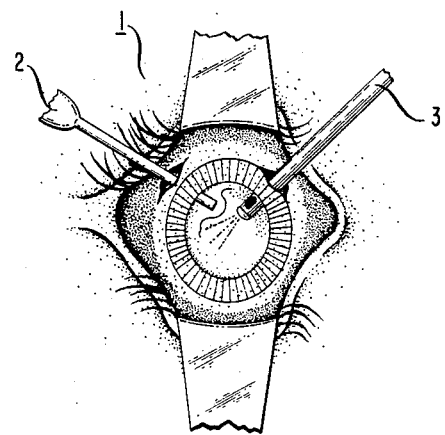
FIGS. 1 and 2 are illustrations of a human eye during intraocular surgery showing a suction cutter being introduced into the cornea for performing operations on the lens, and a lighter-irrigator in accordance with the present invention, being held in irrigating and aspirating positions during the operation.
Figure 2:
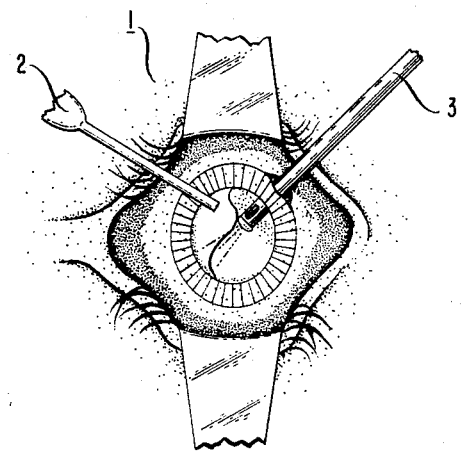

Referring to FIGS. 1 and 2, there is shown a human eye in the process of undergoing a surgical procedure in accordance with the present invention. A suction cutter 2, of a conventional type, is interposed through the corneal walls into the lens area. Simultaneously, a lighter-irrigator in accordance with the present invention is interposed through the corneal wall, from a different direction, to perform the functions of liquid infusion and aspiration as shown in FIGS. 1 and 2, while at the same time providing the level of illumination needed by the surgeon for the operative procedure. FIG. 1 shows a pars plana approach; and FIG. 2 shows an open sky approach.

Figure 3:
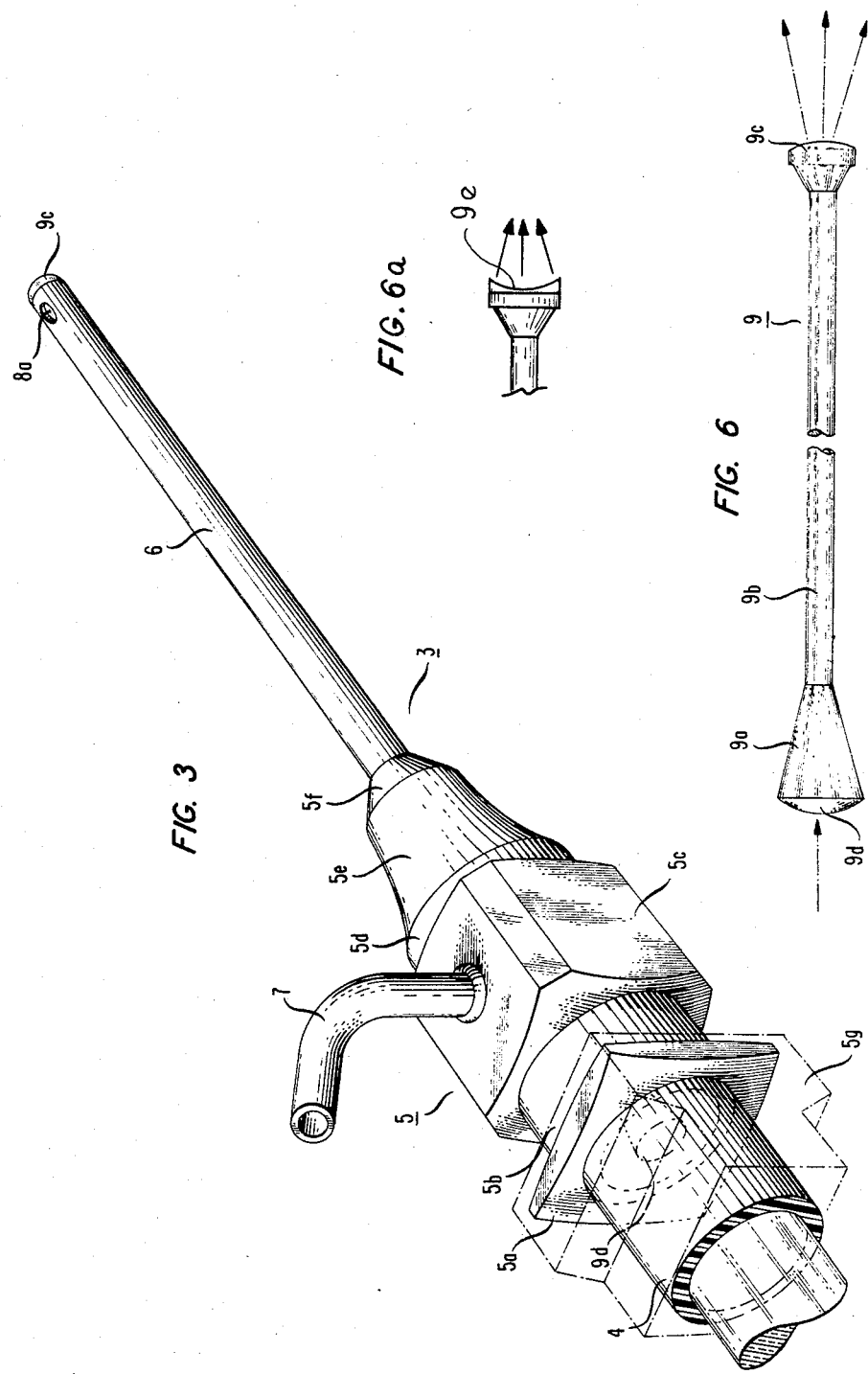
FIG. 3 is a perspective view from the proximal end of a lighter-irrigator in accordance with the present invention, in combination with a light pipe comprising an optic light cord for transmitting light from the source.

Referring to FIG. 3, there is shown an enlarged perspective view of the lighter-irrigator 3 of the present invention, to the proximal end of which is connected the optic light pipe 4.

The latter comprises a translucent lightconducting and dispersing cord of a convenient length which is connected between a conventional source of light and the immediate area of the operative procedure. For example, the light pipe 4 may be of the type generally described in U.S. patent application Ser. No. 261,688, now U.S. Pat. No. 4,422,719, filed on May 7, 1981 by Donald E. Orcutt, the disclosure of which is embraced herein by reference.

For the application disclosed, optimum illumination has been found to be available from a polycarbonate thermoset fiber optic strand which is enclosed in a 0.01 inch thick casing of tetrafluoroethylene having an outer diameter of ⅛ inch. The light entering light pipe 4 at the light source is dispersed all along its path, the balance being conducted to the tip. The rate of dispersion can be controlled during the manufacturing process.

For the present application, it has been found that optimum illumination is available by lateral dispersion from the light pipe 4 to provide adequate work light for the surgical nurses, assistants, and anaesthesiologists by extending the cord to surround the instrument stand, or using a separate light pipe connected to the source for that purpose. By using low level of light during surgery, the surgeon and his assistants can easily locate the instruments in the tray, and can continue to work in the microscope during microsurgery without waiting to become reaccustomed to the darkness. This adjunctive use of the light pipe 4 is of additional convenience, in that its illumination is under control of the operating surgeon, and thus synchronized with the operative procedure. It is contemplated that in certain instances a separate light pipe of the type described can be used by the anaesthesiologist, providing a free end which has the directional properties of a flashlight. Some reduction of light at the illuminating tip is caused by increasing the length of the light pipe, so that it may be necessary to reduce its length, depending on the amount of illumination required for a particular application. Since the light pipe 4 may be formed of a disposable plastic, it can be discarded after a single use, or alternatively, it can be re-sterilized by gas, and reused as a limited-use item. The cover of light pipe 4, which in the present application is preferably made from tetrafluoroethylene, is quite flexible, and can withstand a temperature of 500 degrees Fahrenheit without softening or melting.

Figure 4:
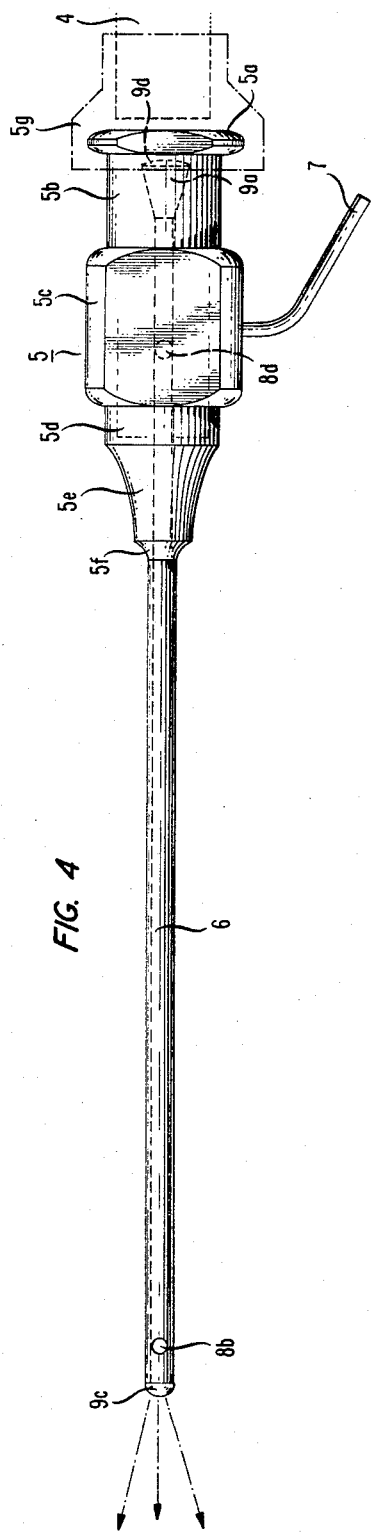
FIG. 4 is a side-elevational view of the lighter-irrigator of the present invention.
Figure 5:
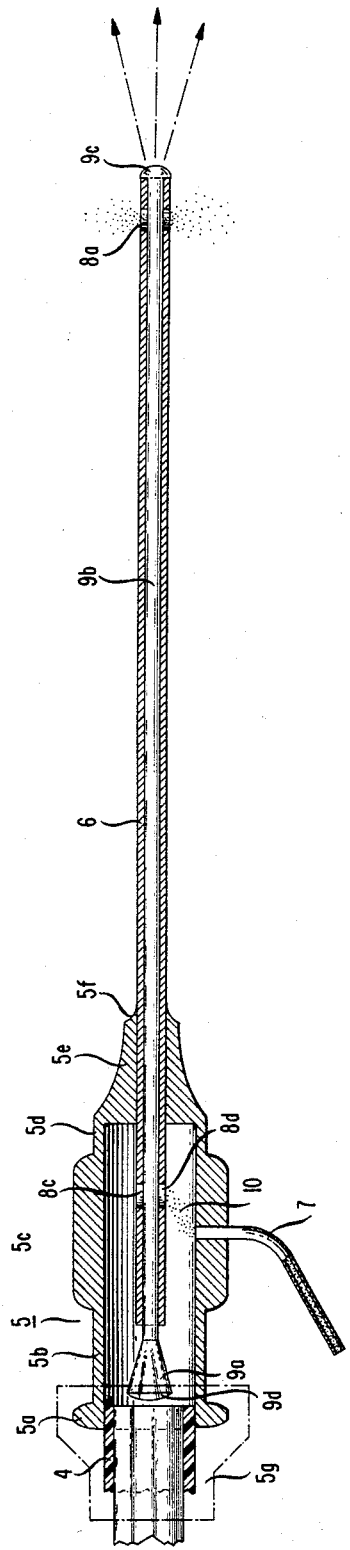
FIG. 5 is a longitudinal sectional view of the lighter-irrigator of the present invention.

Referring to FIG. 3, and to FIGS. 4 and 5 of the drawings, the light pipe 4 is secured in coaxial relation to the lens frame 5a by a standard cannula adapter 5g, at proximal end of the cannula 5, which in the present embodiment comprises a standard Luer lock hub, pre-drilled, of a type well-known in the art. The present embodiment of standard cannula 5 extends 0.7 inch in an axial direction from the rim 5a to the nipple 5f. The rim 5a is connected in coaxial relation to hub 5c through a cylindrical neck 5b. The hub 5c is substantially symmetrical about its principal axis, and is of generally rectangular section, the corners at which the sides are joined being bevelled, forming a substantially rectangular internal cavity. A collar 5d, which is centered on the distal end of hub 5c, is also symmetrical about the axis, and supports a hollow frustoconical protrusion 5e which extends along the axis to a reduced internal diameter terminating in a nipple 5f.

A hypodermic tube 6 of, for example, stainless steel, 2 inches long, and may be either 19 or 20 gauge. In the present example, a 19 gauge tube is used, having an inner diameter of 0.031 inch and an outer diameter of 0.042 inch, providing a wall thickness of 0.0055 inch. This tube is interposed in axial relation into the cannula 5 through the nipple 5f so that it extends 0.6 inch internally, in proximal direction, and 1.4 inches in a distal direction.

Centered on and interposed into one of the sides of the cannula hub 5c, say, 0.35 inch from the input end, is a hose 7, preferably of metal, such as, for example, stainless steel, 0.018 inch in inner diameter. Before hypodermic tube 6 is inserted into cannula 5, at a plane, about 0.04 inch from each its ends are drilled a pair of diametrically opposite holes 8a, 8b at the distal end, and 8c, 8d, at the proximal end. Hose 7 is connected to a source of water solution which may be contained in a conventional hanging bottle, which in the present illustration may comprise, for example, a saline solution of Ringer's lactate, or another saline solution of suitable composition having a 7.4 pH. In the example under description. the water solution flows into the cannula hub 5c and into tube 6 through the holes 8c, and 8d at the proximal end, and out through the two vents 8a, 8b at the distal end, so that it flows into the eye during surgery at the rate of about 15 to 20 cubic centimeters per minute, or at such other rate as is sufficient to maintain the proper liquid pressure for vitreous or intraocular surgery.

Interposed into the proximal end of the cannula 5 so as to extend along the principal axis of the tube 6 is the light guide 9, which is shown in FIG. 6 removed from the the cannula 5 and tube 6.

In the present illustrative example, the light guide 9 comprises an optical fiber of solid polypropylene having an overall length of 2.10 inches, the central portion 9b, for most of its length being, say, 0.018 inch in diameter. The proximal end portion comprises a light funnel 9a which is frustoconical in shape, 0.090 inch in diameter at its outer end, the sides of the cone forming, in section, a 30° angle, symmetrical about the axis, decreasing to a diameter of 0.018 inch at a plane about 0.2 inch back from its proximal end. The round outer face of light funnel 9a is in the form of a convex lens 9d having a focal length sufficient to pick up and focus into light funnel 9a a maximum amount of the light emerging from the end of light pipe 4. The center of the lens 9d is spaced as close as possible to the face of rim 5a, which accommodates the adapter 5g, which in turn, accommodates light pipe 4. Thus, light funnel 9a is disposed to gather the rays of light from the light pipe 4 which are then concentrated in light guide 9b.

During installation of the optic fiber light guide 9 it is placed along the axis of tube 6, being cut off shortly beyond the distal end thereof, and heat-treated at a temperature sufficient to soften and to form a convex bulb or lens having a radius of curvature of, say, 0.5 inch, which fills up and seals against the distal end of the tube 6. Alternatively, the end 9c can be flattened out, or made concave, depending on the light pattern desired at the distal end of the instrument as shown in FIG. 6a at 9e. In any case, the end of tube 6 is sealed, providing an annular space, say, 0.0065 inch wide between the outer surface of light guide 9 and the inner surface of the hypodermic tube 6 in which the liquid solution flows.

Although, for the purposes of a preferred embodiment, the material of light guide 9 has been disclosed as consisting essentially of a solid strand of polypropylene, it will be understood that light guide 9 can be formed of other materials, such as, for example, methyl methocrylate. An important parameter of the material of light guide 9 is that it be optically clear.

The operation of the system is as follows.

Light traveling from a light source (not shown) is transmitted through the light pipe 4, into the lens 9d disposed inside of the rim 5a of cannula 5, at the proximal end of light guide 9, in which it travels down through the light funnel 9a, into the thin light fiber portion 9b, and out the end of the hypodermic tube 9c to supply light into the posterior globe of the eye. The saline water solution to maintain the globe pressure enters from the solution inlet pipe 7 into the hub 5c, from which it enters the hypodermic tube 6 through two holes 8c, 8d, in the side of the tube, travels alongside the small cross-sectional portion of the fiber portion 9b of the light guide to the distal end of tube 6 and is discharged at the tip of the hypodermic tube on the sides, through the holes 8a and 8b.

The light guide 9, which is formed from one piece of light-transmitting material, collects light focused by the lens 9d on the large end, 9a, where it travels within the funnel to supply a large amount of light into a small-diameter portion 9b, of light guide 9. Light emitted from tube 6 lights up the whole end thereof, which light is focused on the operating area by the terminal lens portion 9c, or is dispensed within the globe of the eye, under control of the operating surgeon.

Although the invention has been described with reference to a specific embodiment comprising stated materials and formed to specific dimensions, for the purposes of illustration, it will be understood that the invention is not limited except by the scope of the appended claims.

What is claimed is:

1. A system including, in an operation area, a lighter-irrigator for intraocular and other microsurgery which comprises in combination:

a source of light having a preselected focal area;

a cannula having a hub portion with a relatively wide opening on one end in a plane transverse to and substantially centered on the major axis of the hub of the cannula, said hub opening being disposed in a proximal direction within said focal area of said source of light, at least a portion of said light is directed in the general direction of said major axis, said hub being connected in a distal direction along said axis to a frustoconical member decreasing in internal diameter to a relatively small opening;

a thin-walled elongated hypodermic tube being accommodated in said small opening and extending in a proximal direction internally into the hub of said cannula, and extending for a substantial length axially in a distal direction from said small opening;

a light guide comprising an elongated body of light transmitting material interposed into said cannula extending axially along the interior of said cannula and axially along the length of said hypodermic tube, said light guide terminating at its proximal end in a light funnel of frustoconical shape which laterally seals against and projects beyond the proximal end of said hypodermic tube, said light guide terminating in a light-projecting lens which seals the end of said tube;

a source of liquid for infusion into the said eye during surgery;

a liquid intake pipe for connection to said source of liquid connected into the hub of said cannula;

said hypodermic tube having at least one liquid intake opening near its proximal end in said cannula hub and at least one liquid exhaust opening near its distal end;

an annular space between the light guide and the hypodermic tube forming a channel for transmitting said liquid in a direction substantially parallel to said light guide from said at least one intake opening to said at least one exhaust opening;

a longitudinal fiber optic light pipe for the transmission and dispersion of light which extends from a source substantially spaced-apart from one end of said cannula to a plane adjacent to a relatively larger opening of said cannula, the light from said optic light pipe being substantially focused on said light funnel for concentration on the light transmitting light guide enclosed in said hypodermic tube;

said fiber light pipe comprises in combination:

a flexible core of light transmitting material;

a sleeve of transparent or translucent material tightly surrounding said core in a manner to substantially eliminate air from the interface between said core and said sleeve, said sleeve and said core being constructed and arranged to laterally diffuse, disperse or refract through the sidewall of said sleeve a substantial component of the light transversing said core longitudinally.

2. The combination in accordance with claim 1 wherein said material of said sleeve has an index of refraction which exceeds the index of refraction of the material of said core.

3. The combination in accordance with claim 1 wherein said fiber optic light pipe consists essentially of a thermoset polycarbonate fiber optic bundle having a coating of tetrafluoroethylene.

4. The combination in accordance with claim 1 wherein a lens is interposed between the distal end of said light pipe and the light funnel at the proximal end of said light guide.

5. The combination in accordance with claim 1 wherein the portion of said light guide extended along the axis of said hypodermic tube is less than about 0.018 inch in diameter; wherein the outer diameter of said hypodermic tube is less than about 0.018 inch in diameter; wherein the outer diameter of said hypodermic tube is less than about 0.045 inch; and the wall thickness of said hypodermic tube is less than about 0.004 inch.

6. The combination in accordance with claim 1 wherein said light guide comprises a solid material having optical transmission quality which approximates that of optical quality lens material.

7. The combination in accordance with claim 6 wherein said liquid consists essentially of a saline solution having a pH of approximately 7.4.

8. The combination in accordance with claim 6 wherein said light guide consists essentially of a solid rod of polypropylene.

9. The combination in accordance with claim 1 wherein said light projecting lens at the distal end of said hypodermic tube is substantially convex.

10. The combination in accordance with claim 1 wherein the light projecting lens at the distal end of said hypodermic tube protrudes outwardly in semispherical shape.

11. The combination in accordance with claim 1 wherein the light projecting lens at the distal end of said hypodermic tube is concave.

12. A system including, in an operation area, a lighter-irrigator for intraocular and other microsurgery which comprises in combination:
a source of light having a preselected focal area;
a cannula having a hub portion with a relatively wide opening on one end in a plane transverse to and substantially centered on the major axis of the hub of the cannula, said hub opening being disposed in a proximal direction within said focal area of said source of light, at least a portion of said light is directed in the general direction of said major axis, said hub being connected in a distal direction along said axis to a frustoconical member decreasing in internal diameter to a relatively small opening;
a thin-walled elongated hypodermic tube being accommodated in said small opening and extending in a proximal direction internally into the hub of said cannula, and extending for a substantial length axially in a distal direction from said small opening;
a light guide comprising an elongated body of light transmitting material interposed into said cannula extending axially along the interior of said cannula and axially along the length of said hypodermic tube, said light guide terminating at its proximal end in a light funnel of frustoconical shape which laterally seals against and projects beyond the proximal end of said hypodermic tube, said light guide terminating in a light-projecting lens which seals the end of said tube;
a source of liquid for infusion into the said eye during surgery;
a liquid intake pipe for connection to said source of liquid connected into the hub of said cannula;
said hypodermic tube having at least one liquid intake opening near its proximal end in said cannula hub and at least one liquid exhaust opening near its distal end;
an annular space between the light guide and the hypodermic tube forming a channel for transmitting said liquid in a direction substantially parallel to said light guide from said at least one intake opening to said at least one exhaust opening;
a longitudinal fiber optic light pipe for the transmission and dispersion of light which extends from a source substantially spaced-apart from one end of said cannula to a plane adjacent to a relatively larger opening of said cannula, the light from said optic light pipe being substantially focused on said light funnel for concentration on the light transmitting light guide enclosed in said hypodermic tube;
said longitudinal fiber optic light pipe is extended between the proximal end of said lighter-irrigator and said light source to surround and illuminate other work areas in said operating area in addition to providing a source of light to said lighter-irrigator.

13. A lighter-irrigator for intraocular and other microsurgery which comprises in combination:
a cannula having a hub portion with a relatively wide opening on one end in a plane transverse to and substantially centered on the major axis of the hub of the cannula, said hub being connected in a distal direction along said axis to a frustoconical member decreasing in internal diameter to a relatively small opening;
a thin-walled elongated hypodermic tube being accommodated in said small opening and extending in a proximal direction internally into the hub of said cannula, and extending for a substantial length axially in a distal direction from said small opening;
a light guide comprising a longitudinal fiber optic light pipe for the transmission and dispersion of light which extends from a source substantially spaced apart from one end of said cannula to a plane adjacent to a relatively larger opening of said cannula, the light from said optic light pipe being substantially focused on said light funnel for concentration on the light transmitting light guide enclosed in said hypodermic tube;
a flexible core of light transmitting material;
a sleeve of transparent or translucent material tightly surrounding said core in a manner to substantially eliminate air from the interface between said core and said sleeve, and said core being constructed and arranged to laterally diffuse, disperse or refract through the side wall of said sleeve a substantial component of the light transversing said core longitudinally, where the light guide is interposed into said cannula extending axially along the interior of said cannula and axially along the length of said hypodermic tube, said light guide terminating at its proximal end in a light funnel of frustoconical shape which laterally seals against and projects beyond the proximal end of said hypodermic tube, said light guide terminating in a light-projecting lens which seals the end of said tube and is designed to project light beyond the end of said tube;

a liquid intake pipe for connecting a source of liquid into the hub of said cannula;

said hypodermic tube having at least one liquid intake opening near its proximal end in said cannula hub and at least one liquid exhaust opening near its distal end;

an annular space between the light guide and the hypodermic tube forming a channel for transmitting said liquid in a direction substantially parallel to said light guide from said at least one intake opening to said at least one exhaust opening.

14. The combination in accordance with claim 13 wherein the portion of said light guide extended along the principal axis of said hypodermic tube is less than about 0.018 in diameter; wherein the outer diameter of said hypodermic tube is less than about 0.045; and the wall thickness of said hypodermic tube is less than about 0.0004.

15. The combination in accordance with claim 14 wherein said light guide comprises a solid material having optical transmission quality which approximates that of optical lens material.

16. The combination in accordance with claim 15 wherein said light guide consists essentially of a solid rod of polypropylene.

17. The combination in accordance with claim 13 wherein said light projecting lens at the distal end of said hypodermic tube is substantially convex.

18. The combination in accordance with claim 13 wherein the light projecting lens at the distal end of said hypodermic tube protrudes outwardly in semispherical shape.

19. The combination in accordance with claim 13 wherein the light projecting lens at the distal end of said hypodermic tube is substantially concave.

20. The method of performing intraocular surgery which comprises making two incisions through the cornea at sites substantially spaced-apart;

utilizing one of said incisions for interposing cutting means and aspiration means; and utilizing the other of said incisions for interposing a light-irrigator which comprises a thin-walled hypodermic tube connected to convey a stream of liquid along a path in said tube and into the eye for maintaining the liquid pressure therein during surgery, said hypodermic tube including a light-transmitting light guide for collecting and concentrating light from a source of light into said hypodermic tube and for transmitting said light along a path substantially parallel to said liquid path to the distal end of said tube for illuminating the area of said surgery.

* * * * *